United States Patent
Min et al.

(10) Patent No.: US 7,381,819 B2
(45) Date of Patent: Jun. 3, 2008

(54) COMPOSITION FOR TREATMENT OR PREVENTION OF ENDOMETRIAL CANCER AND METHOD OF PREVENTING OR TREATING ENDOMETRIAL CANCER USING THE COMPOSITION

(75) Inventors: Churl Ki Min, Suwon (KR); Dong Soon Choi, Suwon (KR)

(73) Assignee: Ajou University Industry Cooperation Foundation, Suwon (KR)

( * ) Notice: Subject to any disclaimer, the term of this patent is extended or adjusted under 35 U.S.C. 154(b) by 67 days.

(21) Appl. No.: 11/207,739

(22) Filed: Aug. 22, 2005

(65) Prior Publication Data

US 2006/0264396 A1   Nov. 23, 2006

(30) Foreign Application Priority Data

May 18, 2005  (KR)  .................... 10-2005-0041766

(51) Int. Cl.
| | |
|---|---|
| C07H 21/02 | (2006.01) |
| C07H 21/04 | (2006.01) |
| C12Q 1/68 | (2006.01) |
| C12P 19/34 | (2006.01) |
| C12N 5/00 | (2006.01) |
| C12N 5/02 | (2006.01) |

(52) U.S. Cl. .................... 536/24.5; 536/23.1; 536/24.3; 536/24.33; 435/6; 435/91.1; 435/325; 435/375

(58) Field of Classification Search ................ 536/23.1, 536/24.3, 24.33, 24.5; 514/44
See application file for complete search history.

(56) References Cited

U.S. PATENT DOCUMENTS 5,422,243 A    6/1995 Jalkanen et al.

FOREIGN PATENT DOCUMENTS

| WO | WO 01/75164 A2 | 10/2001 |
|---|---|---|
| WO | WO 03/006477 A1 | 1/2003 |

OTHER PUBLICATIONS

Lu et al. (2005). Deliverying siRNA in vivo for functional genomics and novel therapeutics. From RNA Interference Technology (Cambridge, Appasani, ed., pp. 303-317).*

Samarsky et al. (2005). RNAi in drug development: Practical considerations. From RNA Interference Technology (Cambridge, Appasani, ed., pp. 384-395).*

Downward, J. Science, medicine, and the future. RNA interference. BMJ, 2004 vol. 328:1245-1248.*

Paroo et al. Challenges for RNAi in vivo. Trends in Biotechnology, 2004 vol. 22:390-394.*

Matsuzaki et al. Reduced syndecan-1 expression stimulates heparin-binding grwoth factor-mediated invasion in ovarian cancer cells in a urokinase-independent mechanism. Oncology Reports, 2005 vol. 14:449-457.*

Inki, Pirjo, "Expression of Syndecan-1 in Female Reproductive Tract Tissues and Cultured Keratinocytes," *Molecular Human Reproduction*, 3(4):299-305, 1997.

* cited by examiner

*Primary Examiner*—Sean McGarry
*Assistant Examiner*—Terra Cotta Gibbs
(74) *Attorney, Agent, or Firm*—Rothwell, Figg, Ernst & Manbeck (57) ABSTRACT

Provided are a composition for the treatment or prevention of an endometrial cancer including a nuclear acid molecule inducing RNA interference against human syndecan-1 gene expression and a pharmaceutically acceptable carrier, and a method of treating or preventing an endometrial cancer including administering the composition to an individual.

3 Claims, 5 Drawing Sheets

SEQUENCE LISTING

<160> NUMBER OF SEQ ID NOS: 6

<210> SEQ ID NO 1
<211> LENGTH: 58
<212> TYPE: RNA
<213> ORGANISM: Artificial Sequence
<220> FEATURE:
<223> OTHER INFORMATION: shRNAi1 against human syndecan-1 gene
      expression

<400> SEQUENCE: 1
gggagugaua gucuuuugcu ucuugcuuca agcaaaagac uaucacuccc uauaguga        58

<210> SEQ ID NO 2
<211> LENGTH: 64
<212> TYPE: RNA
<213> ORGANISM: Artificial Sequence
<220> FEATURE:
<223> OTHER INFORMATION: shRNAi2 against human syndecan-1 gene
      expression

<400> SEQUENCE: 2
gggauaucac cuugucacag cagacuugcu ucucugcugu gacaagguga uaucccuaua        60
guga        64

<210> SEQ ID NO 3
<211> LENGTH: 58
<212> TYPE: RNA
<213> ORGANISM: Artificial Sequence
<220> FEATURE:
<223> OTHER INFORMATION: control shRNAi1 against human syndecan-1 gene
      expression

<400> SEQUENCE: 3
gguguagaua gguuuccguu ucuugcuuca aacggaaacc uaucuacacc uauaguga        58

<210> SEQ ID NO 4
<211> LENGTH: 64
<212> TYPE: RNA
<213> ORGANISM: Artificial Sequence
<220> FEATURE:
<223> OTHER INFORMATION: control shRNAi2 against human syndecan-1 gene
      expression

<400> SEQUENCE: 4
ggggacuuca accguuuaag caaccuugcu ucguugcuua aacgguugaa gucccuaua        60 guga        64

<210> SEQ ID NO 5
<211> LENGTH: 20
<212> TYPE: DNA
<213> ORGANISM: Artificial Sequence
<220> FEATURE:
<223> OTHER INFORMATION: forward primer for syndecan-1 gene
      amplification

<400> SEQUENCE: 5
gagcaggact tcacctttga        20

<210> SEQ ID NO 6
<211> LENGTH: 20
<212> TYPE: DNA
<213> ORGANISM: Artificial Sequence
<220> FEATURE:

-continued

```
<223> OTHER INFORMATION: reverse primer for syndecan-1 gene
      amplification

<400> SEQUENCE: 6
tgcttcagtt tggagaaacc                                              20
```

COMPOSITION FOR TREATMENT OR PREVENTION OF ENDOMETRIAL CANCER AND METHOD OF PREVENTING OR TREATING ENDOMETRIAL CANCER USING THE COMPOSITION

CROSS-REFERENCE TO RELATED PATENT APPLICATION

This application claims priority from Korean Patent Application No. 10-2005-0041766, filed on May 18, 2005, in the Korean Intellectual Property Office, the disclosure of which is incorporated herein in its entirety by reference.

1. Field of the Invention

The present invention relates to a composition for the treatment or prevention of an endometrial cancer including small hairpin RNA molecules and a method of treating or preventing an endometrial cancer using the composition.

2. Description of the Related Art

RNA interference (RNAi) in animals and lower eukaryotes, quelling in fungi, and posttranscriptional gene silencing (PTGS) in plants are families of the phenomenon commonly referred to as RNA silencing. Common characteristics of the RNA silencing phenomena generate short RNAs (21-26 nt) acting as specific determinants for down-regulation of gene expression and require Argonaute family proteins (or referred to as specific PAZ and Piwi Domain (PPD) proteins).

Short RNAs are produced in animals by a member of the Dicer family which is dsRNA-specific endonuclease. Members of the Dicer family are large multidomain proteins including putative RNA helicase, PAZ, two adjacent RNaseIII domains, and at least one dsRNA-binding domain. The adjacent RNaseIII domains are regarded to mediate the endonucleolytic cleavage of dsRNAs into small interfering RNAs (siRNAs) which are mediators of RNAi. In Drosophilae and mammals, siRNAs, in cooperation with at least one Argonaute family protein, form RNA-induced silencing complexes (RISCs) known as protein-RNA complexes and mediate the cleavage of target RNA sequences having a significant homology with the siRNAs.

In addition to the Dicer and Argonaute proteins, the RdRP gene for RNA-dependent RNA polymerase is necessary for RNA silencing in *Caenorhapditis elegans, Neurospora crassa*, and *Dictyostelium discoideum*, but appears unnecessary for the RNAi in Drosophilae or mammals. In plants, putative RdRP and SGS2 are necessary for PTGS initiated by transgene overexpressing endogeneous mRNAs. However, transgene designed to produce dsRNAs may not require putative RdRP and SGS2 for PTGS. Similarly, SGS2 is not required for silencing induced by viral replication (virus-induced gene silencing, VIGS) through dsRNA intermediates.

Dicer in animals and CARPEL FACTORY (CAF, Dicer homologue) in plants produce MicroRNAs (miRNAs), i.e., single-stranded, noncoding RNAs (20-24 nt in length) which are presumed to be endogeneous mRNA expression regulators. The miRNAs are produced by Dicer cleavage of transcripts of stem-loop precursor RNAs. The miRNAs may be positioned at 5' or 3' of the strands of double-stranded stems. In animals, pre-miRNAs are transcribed into long primary transcripts (pri-miRNAs) which are then processed into pre-miRNAs having a compact and folded structure in nuclei and then into mature miRNAs by Dicer cleavage in cytoplasms. Animal miRNAs are partially complementary to target mRNAs. Thus, it seems that that the miRNAs inhibit the translation of the target mRNAs rather than induce direct cleavage of the target mRNAs by RNAi pathway. It seems that plant miRNAs mediates the cleavage of target RNAs through RNAi-analogous mechanism due to their higher complementarity with cellular mRNAs.

Generally, techniques of constructing nucleic acid molecules inducing the RNAi against target gene expression are well known in the art. For example, WO03/006477 discloses a nucleic acid molecule including a regulatory sequence linked to a nucleic acid sequence that encodes a RNA precursor, the RNA precursor including a first stem portion including a sequence of at least 18 nucleotides complementary to target mRNA, a second stem portion including a sequence of at least 18 nucleotides that is sufficiently complementary to the first stem portion to hybridize with the first stem portion to form a duplex stem, and a loop portion connecting the two stem portions. WO 2001/75164 discloses RNA segments (21-23 nucleotides in length) mediating the RNAi against corresponding mRNAs. RNAi-inducing nucleic acid molecules can also be constructed using a commercially available kit for construction of nucleic acid molecules inducing the RNAi against target gene expression (e.g., MessageMuter™ shRNAi Production Kit, manufactured by Epicentre).

Figure 1:
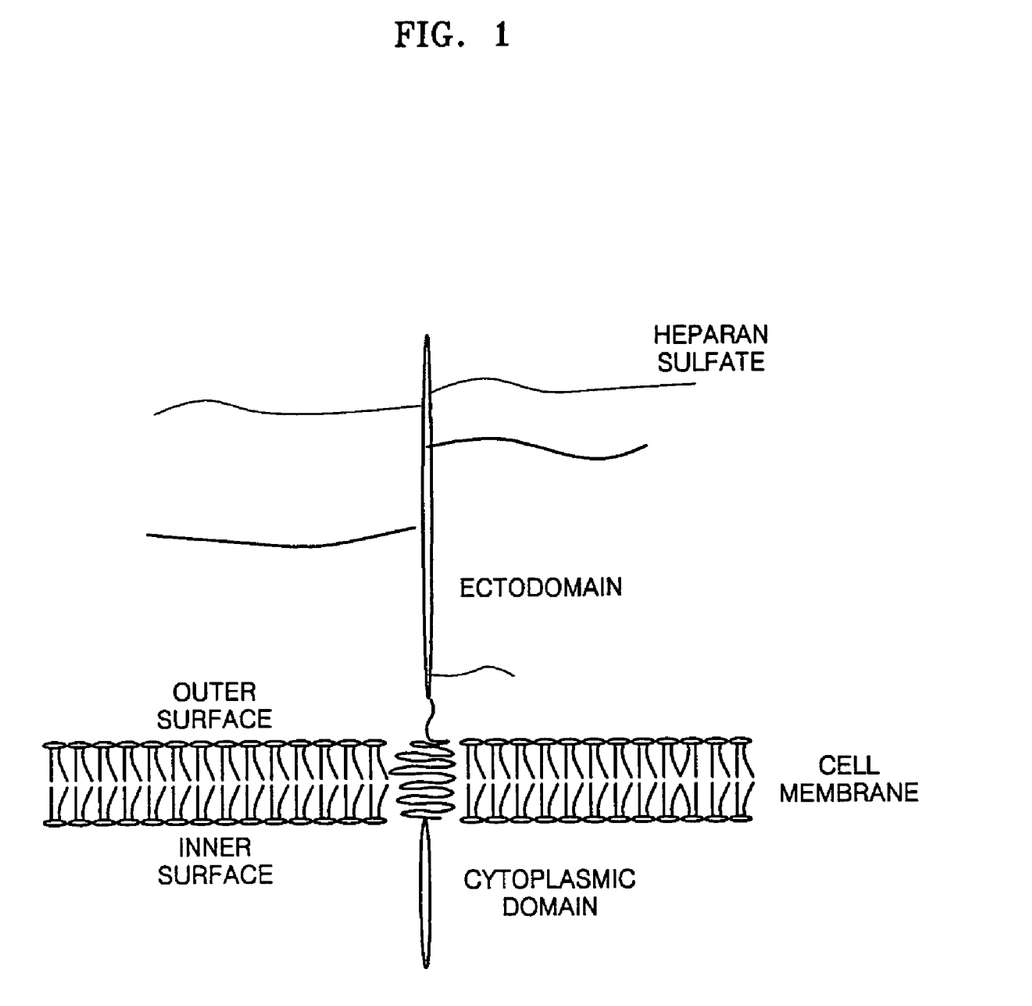
FIG. 1 is a diagram illustrating the molecular structure of human syndecan-1.

Syndecan is known as a cell surface proteoglycan participating in cell regulation by matrix recognition and binding with a growth factor. Syndecan-1 is a proteoglycan binding with collagen, fibronectin, and FGF-2, and also participating in cell attachment (see FIG. 1). FIG. 1 is a diagram illustrating the structure of syndecan-1 protein. The syndecan-1 protein is composed of cytoplasmic domain, transmembrane domain, and ectodomain. The ectodomain includes heparan sulfate (HS). During embryogenesis, the syndecan-1 is first detected inside cells at the four-cell stage, and is expressed in mesenchymal and epithelial cells in a highly developmentally regulated manner. At the later stage, the syndecan-1 is almost predominantly expressed in epithelial cells except plasma cells and Leydig cells. Oncogenesis is associated with remarkable downregulation of syndecan-1 expression (Molecular Human Reproduction vol 3. no 4 pp. 299-305, 1997). U.S. Pat. No. 5,422,243 discloses a method for detecting a malignant or premalignant state of human cells that express syndecan in a non-malignant state by detecting an absence or an expression reduction of a syndecan protein or mRNA.

As described above, according to convention techniques, underexpression of the syndecan is associated with oncogenesis. Unlike these conventional techniques, the present inventors surprisingly found that shRNAi-mediated silencing of syndecan-1 expression in endometrial cancer cells could inhibit the growth of tumors, and thus completed the present invention.

SUMMARY OF THE INVENTION

The present invention provides a composition for the treatment or prevention of an endometrial cancer including a nucleic acid molecule inducing the RNA interference against human syndecan-1 gene expression.

The present invention also provides a method of treating or preventing an endometrial cancer using the composition.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention provides a composition for the treatment or prevention of an endometrial cancer including a nucleic acid molecule inducing the RNA interference against human syndecan-1 gene expression and a pharmaceutically acceptable carrier.

Generally, techniques for constructing a nucleic acid molecule inducing the RNA interference against target gene expression are well known in the art. The nucleic acid molecule inducing the RNA interference against the human syndecan-1 gene expression in the composition of the present invention can be constructed by any method known in the art, for example, by a method disclosed in WO03/006477, but the present invention is not limited thereto. The nucleic acid molecule of the present invention can also be constructed using a commercially available kit for constructing a nucleic acid molecule inducing the RNA interference against target gene expression (e.g., MessageMuter™ shRNAi Production Kit, manufactured by Epicentre).

As used herein, the term "nucleic acid molecule" is intended to embrace RNA, DNA, and a nucleic acid analogue such as PNA. The nucleic acid molecule inducing the RNA interference is not particularly limited provided that it can induce the RNA interference against human syndecan-1 gene expression. For example, the nucleic acid molecule inducing the RNA interference includes a short interfering nucleic acid (siNA), a short interfering RNAi (siRNAi), MicroRNA (miRNA), and a short hairpin RNAi (shRNAi). Preferably, the nucleic acid molecule inducing the RNA interference is shRNAi.

In an embodiment of the present invention, the nucleic acid molecule inducing the RNA interference may be a RNA molecule as set forth in SEQ ID NO: 1 or 2. The RNA molecule of SEQ ID NO: 1 is a shRNAi molecule having a sequence of 18 nucleotides complementary to the 3'-UTR (position: 2404-2422) of the human syndecan-1 gene (NCBI Accession No. NM_002997), and the RNA molecule of SEQ ID NO: 2 is a shRNAi molecule having a sequence of 18 nucleotides complementary to the coding region (position: 459-480) of the human syndecan-1 gene (NCBI Accession No. NM_002997)

In another embodiment of the present invention, the nucleic acid molecule inducing the RNA interference may be an expression vector including a DNA encoding the RNA molecule as set forth in SEQ ID NO: 1 or 2.

In the present invention, since the expression vector contains the DNA encoding the RNA molecule having the sequence of SEQ ID NO: 1 or 2, when the expression vector is transfected into an eukaryotic cell, the DNA can be transcribed into the RNA molecule having the sequence of SEQ ID NO: 1 or 2 by the transcription system in the eukaryotic cell. The expression vector may contain a transcriptional regulatory sequence operably linked to the DNA encoding the RNA molecule having the sequence of SEQ ID NO: 1 or 2. The expression vector may be any expression vector known in the art. For example, the expression vector may be a plasmid or a plasmid-derived vector, a bacteriophage or a bacteriophage-derived vector, or a plant- or animal-derived viral vector, but the present invention is not limited thereto. Examples of the animal-derived viral vector include an adenovirus-associated viral vector and a vaccinia virus-derived vector.

In the present invention, the human syndecan-1 gene may be the gene of NCBI Accession No. NM_002997, but the present invention is not limited thereto. Those of ordinary skill in the art could select a variant having substantially the same activity as syndecan-1. It should be understood that the syndecan-1 variant is within the scope of the present invention.

Generally, it is known that the syndecan-1 is almost predominantly expressed in epithelial cells except plasma cells and Leydig cells. It is also known that malignant tumor formation is associated with remarkable downregulation of syndecan-1 expression (Molecular Human Reproduction vol 3. no 4 pp. 299-305, 1997). Unlike these known techniques, the present inventors surprisingly found that RNA interference-medicated downregulation of syndecan-1 expression in endometrial cancer cells could inhibit the growth of tumor cells. Thus, the composition of the present invention can be used in the prevention and/or treatment of an endometrial cancer by inhibiting human syndecan-1 gene expression by inducing the RNA interference against the human syndecan-1 gene expression.

As used herein, the term "pharmaceutically acceptable carrier" is meant to embrace a solvent, a dispersion medium, a coating agent, an antibacterial or antimicrobial agent, an isotonic solution, and a sustained release agent which are suitable for pharmaceutical administration. The use of a pharmaceutically acceptable carrier for a pharmaceutically active substance is well known in the art.

A pharmaceutically acceptable diluent or carrier that can be used in the composition of the present invention may be at least one selected from an excipient, a disintegrating agent, a binder, and a lubricant. For example, when the composition of the present invention is prepared in the form of a solid formulation such as a tablet or a hard capsule, it may contain an excipient such as microcrystalline cellulose, lactose, and low-substituted hydroxycellulose; a disintegrating agent such as sodium starch glycolate or calcium monohydrogen phosphate (anhydrous); a binder such as polyvinylpyrrolidone, low-substituted hydroxypropylcellulose, or hydroxypropylcellulose; and a lubricant such as magnesium stearate, silicon dioxide, or talc.

An additive imparting gloss to a tablet, such as anhydrous dibasic calcium phosphate, may be used. A tablet may also be coated with a water-insoluble material to prevent the infiltration of moisture in air into the tablet. At this time, the coating material should have a compact molecular structure and may not be easily dissolved in an aqueous solution. Thus, the coating material may be a polymer material such as a methacrylic acid copolymer, hydroxypropylmethylcellulosephthalate, celluloseacetatephthalate, hydroxypropylmethylcelluloseacetatesuccinate, and polyvinylalcohol. These polymer materials may be used alone or in combination. A coating layer coated on a tablet may include an additive for a coating material commonly known in the art, e.g., a plasticizer, a preservative, a pigment, or a light shielding agent.

A supplementary active ingredient such as a protein, an antibody, and a regulating compound may also be incorporated into the composition of the present invention.

The pharmaceutical composition of the present invention can be appropriately formulated according to a desired administration form. The pharmaceutical composition of the present invention may be administered parenterally (e.g., intravenously, intracutaneously, subcutaneously, intraperitonealy, or intramuscularly), orally (e.g., inhalation), transdermally (tropically), or transmucosally. A solution or suspension administered parenterally, intracutaneously, or subcutaneously may contain the following ingredients: a sterile diluent such as injectable solution, a salt solution, fixed oil, polyethyleneglycol, glycerine, propyleneglycol or other synthetic solvent; an antibacterial agent such as benzylalcohol or methylparabene; an antioxidant such as ascorbic acid or sodium bisulfate; a chelating agent such as EDTA; a buffer such as acetate, citrate, or phosphate; and a tonicity adjusting agent such as sodium chloride or glucose. The pH of the composition may be adjusted by an acid or a base such as hydrochloric acid or sodium hydroxide. A parenterally administered formulation may be packaged in glass or plastic ampules, disposable injection devices, or multi-dose vials. The pharmaceutical composition of the present invention may be formulated as a suppository (e.g., together with a common suppository base such a cocoa butter or other glyceride).

To ensure easy administration and dosage uniformity, it is particularly preferable that an oral or parenteral composition is formulated as a dosage unit form. The "dosage unit" means a physical unit of an optimal amount taken at one time for the treatment of an individual, i.e., a unit containing the predetermined amount of an active ingredient designed to produce a desired drug effect in association with a desired pharmaceutical carrier.

The unit dosage of the nucleic acid molecule of the present invention may be determined by standard pharmaceutical procedures in cell cultures or experimental animals such as a procedure of determining LD50 (the dose lethal to 50% of the population) and ED50 (the dose that produces a drug effect in 50% of the population). The dose ratio between toxic and therapeutic effects is the therapeutic index and may be represented by the ratio LD50/ED50. Compounds which exhibit large therapeutic indices are preferred.

The data obtained from the cell culture assays and animal studies can be used in formulating a range of dosage for use in humans. Preferably, the dosage of such compounds lies within a range of circulating concentrations that include the ED50 with little or no toxicity. The dosage may vary within this range depending upon the dosage form employed and the route of administration utilized.

A therapeutically effective amount of the nucleic acid molecule inducing the RNA silencing of the human syndecan-1 gene used in the composition of the present invention may be in the range from 0.0001 µg to 100 mg/day, preferably from 0.001 µg to 10 mg/day, and more preferably from 0.01 µg to 1 mg/day.

The present invention also provides a method of treating or preventing an endometrial cancer including administering a composition of the present invention to an individual.

The composition of the present invention, and the administration method and dosage of the composition are as described above.

Hereinafter, the present invention will be described more specifically with reference to the following examples. The following examples are for illustrative purposes and are not intended to limit the scope of the invention.

EXAMPLES

Material and Method

The materials and methods used in the examples were as follows.

1. Cell Transfection

To efficiently perform cell transfection, 1,000 to 10,000 cells were inoculated into wells of 24- and 6-well plates, incubated for 24 hours, and transfected according to the manufacturer's instructions (Mirus, America). In brief, Transit-TKO transfection reagent (Mirus, America) was pre-mixed with RPMI-1640 serum-free medium for 15 minutes according to the manufacturer's instructions. Then, an appropriate amount of shRNAi were mixed with the TKO solution and incubated for 15 minutes. Then, the mixture was uniformly added to each well so that the final concentration of each of test shRNAi and control shRNAi molecules was 50 nM.

2. Immunohistochemical and Immunocytochemical Experiments

Anti-human syndecan-1 monoclonal antibody was commercially purchased from Santacruz (America) and Cymbus Biotechnology (America). Endometrial cancer tissues were collected during the period ranging from 1995 to 2003, and 43 endometrial cancer tissues were used. Follow-up tests were performed during 4 months to 9 years (mean: 48 months). 34 endometrial cancer tissues with a grade 1 malignancy and 9 endometrial cancer tissues with a grade 2 or more malignancy were used.

The obtained data were statistically analyzed using Student-t test and Mann-Witney U test.

A detailed experimental procedure was as follows. 10,000 cells were inoculated onto wells of a 24-well plate, and transfected as described above. At 72 hours post-transfection, the cells were fixed with 3.7% formalin in PBS at 4° C. overnight and washed three times for 5 minutes. After washing, a −20° C. cold methanol was added to the cells for 3 minutes, and the cells were then washed with PBS three times for 5 minutes. Then, the cells were treated with a 3% hydrogen peroxide solution for 5 minutes and washed with PBS three times. Anti-human syndecan-1 mouse monoclonal antibody diluted to 1/1,000 was applied to the cells at 25° C. for 2 hours, and the cells were then washed with PBS three times. After the washing, the cells were treated with Histostain-Plus (Zymed, America) according to the manufacturer's instructions for secondary antibody conjugation. Finally, the cells were treated with stable DAB (Invitrogen, America) until they were visualized.

3. RT-PCR 100,000 cells were inoculated onto wells of a 6-well plate, and transfected as described above for RT-PCR. At three days post-transfection, for each well, the cells were solubilized with 1 ml of TRIzol reagent (Invitrogen, America) to extract total RNAs. The RNA extraction was performed according to the manufacturer's instructions. All RNAs had a 260/280 nm absorbance ratio of 1.9 or more. 5 µg of each total RNA sample was reverse-transcribed with MMuLV reverse transcriptase (Bioneer, Korea). Then, PCR was performed using syndecan-1 specific primers (SEQ ID NOS: 5 and 6) and Taq Premix (Bioneer, Korea). PCR results for beta-actin demonstrated that RT-PCR was normally performed.

4. Gene Knockout Using shRNAi (Small Hairpin Interfering RNA)

To obtain optimal knockout results, 6 types of shRNAi molecules were constructed using MessageMuter™ shRNA Production Kit (Cat No. MM031110, EPICENTRE, America) and the effects thereof were tested. Each type of the shRNAi molecules was diluted to a final concentration of 50 nM. Control shRNAi was designed by scrambling the shRNAi sequence. All the types of the shRNAi molecules thus constructed exhibited syndecan-1 specificity.

Among the 6 types of the shRNAi molecules, shRNAi1, shRNAi2, control shRNAi1, and control shRNAi2 molecules had sequences as set forth in SEQ ID NOS: 1-4, respectively.

5. Cell proliferation was assessed using MTT analysis (Roche, America). Absorbance was measured at 570/650 nm.

6. Invasion assay was performed using matrigel-coated inserts (Millipore, America) having 12 μm-sized pores.

7. Cell growth assay was performed in a 96-well format in an unattached state. Absorbance was measured at 570/650 nm.

Example 1

Detection of Overexpression of Syndecan-1 in Endometrial Cancer Cells

In this Example, to ascertain the truth of the conventional report that oncogenesis is associated with the downregulation of syndecan-1 expression, the expression level of syndecan-1 in endometrial cancer cells was determined.

The expression level of syndecan-1 was determined by extracting endometrial cancer tissues from hyperplasia to stage III endometrial cancer patients followed by staining with anti-syndecan-1 antibody (Santacruz or Cymbus Biotechnology, America). The advanced stage (grade) of the endometrial cancer was determined on sets of the same paraffin sections of the same tissues stained with hematoxylin and eosin.

Figure 2:
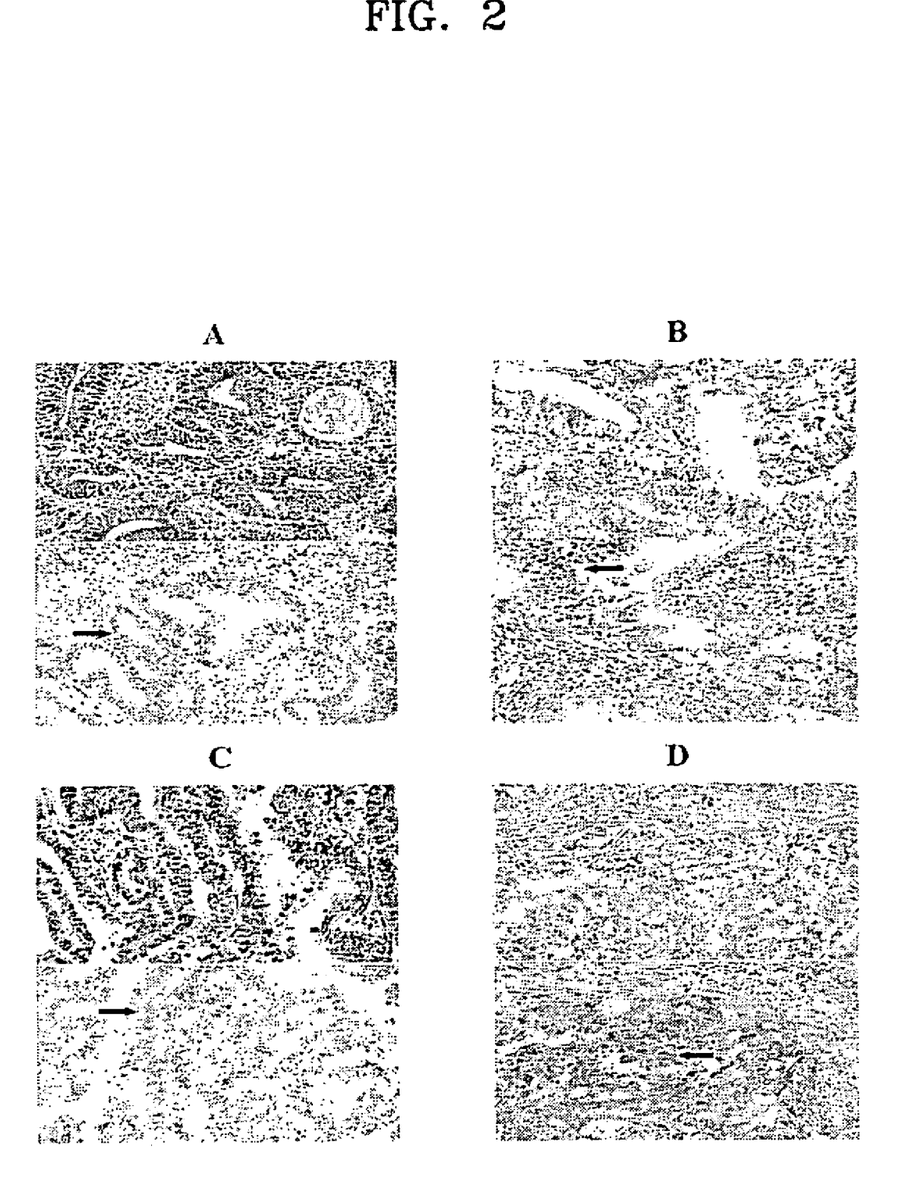
FIG. 2 shows immunohistochemical staining results using anti-syndecan-1 antibody for tumor cells of endometrial cancer tissues extracted from endometrial cancer patients (Santacruz, America)

The results are shown in FIG. 2. As shown in FIG. 2, overexpression of syndecan-1 in the endometrial cancer cells was observed, which is in contrast to the conventional report. An arrow represented in FIG. 2 indicates a positive staining of syndecan-1 in the cancer tissues.

Assessed statistical data are presented in Table 1 below.

TABLE 1

| Variable | P-value | Analysis method |
|---|---|---|
| Tumor stage (grade) | 0.043 | Student t-test |
| Invasion depth | 0.012 | |
| Surgical stage | 0.039 | |
| Combined cancer | 0.014 | Mann-Whitney U test |
| Lymphatic vascular space | 0.009 | |

Example 2

Construction of shRNAi Against Human Syndecan-1

There were constructed shRNAi molecules having a sequence of 18 nucleotides complementary to each of the coding region and the 3'-UTR of human syndecan-1 gene having a sequence of NCBI Accession No. NM_002997. For this, a commercially available kit (MessageMuter™ shRNAi Production Kit, Cat No. MM031110, EPICENTRE, America) was used.

In detail, the shRNAi molecules were constructed according to the following procedure.

(1) Selection of Candidate Target Sequences

The target sequences of the shRNAi molecules were predicted using software on web, Easy siRNA and shRNA Sequence Selector. Six target candidates were selected from the predicted target sequences according to the instructions disclosed in the manual (MessageMuter™ shRNAi Production Kit, Cat No. MM031110, EPICENTRE, America). A hairpin loop sequence (CTTGCTTC) and its complementary sequence were added to 3'-ends of complementary two strands of each selected target candidate sequence. T7 promoter oligo sequence (TATAGTGA) was added to 3'-ends of the complementary two strands. Then, templates were synthesized to be used for in vitro production of shRNAi (Genotech, Korea).

(2) Annealing

The templates were diluted to 50 μM, and then annealed. Reaction mixture for each template:

1.5 ml (75 pmole) T7 promoter Oligo
1 ml (50 pmole) user-designed Oligo
2 ml 5× annealing buffer
5.5 ml RNase-free water Each reaction mixture was incubated at 75° C. for two minutes and cooled to room temperature for two minutes.

(3) Fill-In Reaction

Fill-in reaction was performed according to the manual. Each reaction mixture:

10 ml each annealed product
2 ml 10× Klenow Fill-in buffer
2 ml dNTP mix (2.5 mM for each dNTP)
1 ml Exo-Minus Klenow DNA polymerase (20 Unit/ml)
5 ml RNase-free water Each reaction mixture was incubated at 37° C. for 30 minutes, heated to 70° C. for 10 minutes to inactivate the enzyme, and then cooled to room temperature.

(4) In Vitro Transcription shRNAi molecules were constructed from the six templates according to the manual.

Each reaction mixture:

2.8 ml RNase-free water
4 ml Exo-Minus Klenow DNA polymerase "Fill-in product"
2 ml AmplScribe T7-Flash 10× reaction buffer
7.2 ml NTP mix (25 mM for each dNTP)
2 ml 100 mM DTT
2 ml AmpliScribe T7-Flash Enzyme solution Each reaction mixture was cultured at 42° C. for 90 minutes to produce shRNAi.

(5) Purification and Resuspension of shRNAi

The shRNAi molecules were purified with phenol/chloroform and precipitated with 100% ethanol. Then, shRNAi pellets were washed with 70% ethanol, centrifuged, and dried. The shRNAi molecules were resuspended in a shR-NAi protecting solution, diluted to 50 μM, and stored at −80° C. until use.

As a result, six types of shRNAi molecules were obtained. Among them, only two types silenced syndecan-1 gene expression in the cell culture experiments, and had nucleotide sequences as set forth in SEQ ID NOS: 1 and 2, respectively.

Example 3

Knockout of Syndecan-1 Gene Expression Using shRNAi

In this Example, the shRNAi molecules constructed in Example 2 were injected into tumor cells of endometrial cancer tissues, and the expression level of human syndecan-1 gene was determined. The expression level of human syndecan-1 gene was determined by an immunohistochemical method and RT-PCR.

Figure 3:
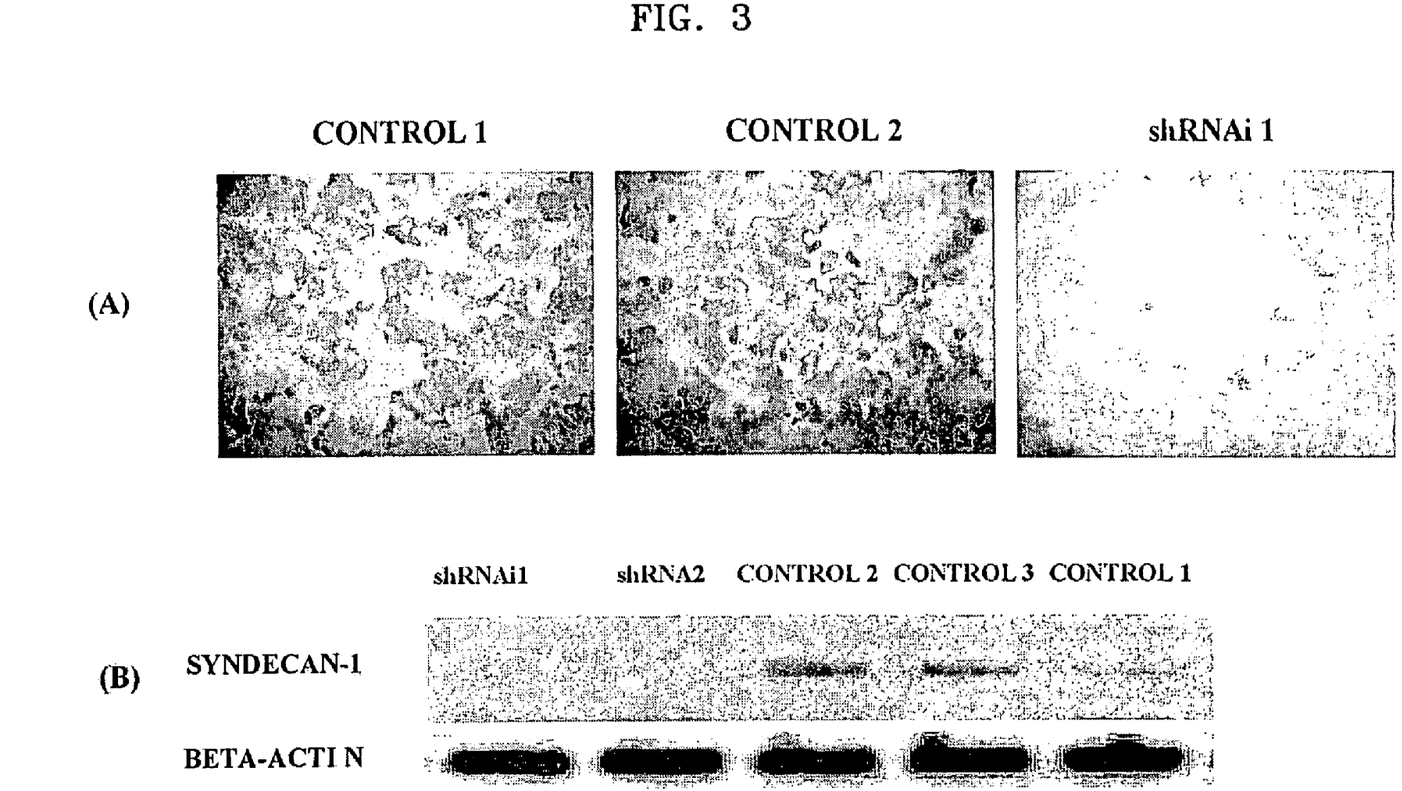
FIG. 3 shows immunohistochemical staining results using anti-syndecan-1 mouse monoclonal antibody for shRNAi-transfected endometrial cancer cells (A) and RT-PCR results for total RNAs derived from the endometrial cancer cells using syndecan-1 gene specific primers (B)

The results are shown in FIG. 3. In FIG. 3, (A) shows immunohistochemical staining results using anti-syndecan-1 mouse monoclonal antibody for endometrial cancer cells transfected with shRNAi for three days in a 24-well plate. In (A) of FIG. 3, "control 1" is cells treated with only a transfection reagent, and "control 2" is cells treated with control shRNAi1 having a nucleotide sequence of SEQ ID NO: 3. Referring to (A) of FIG. 3, knockout of syndecan-1 occurred by shRNAi. In FIG. 3, (B) shows the results of RT-PCR using syndecan-1 specific primers (SEQ ID NOS: 5 and 6) for cDNAs synthesized from total RNA molecules isolated from cells containing shRNAi1 and 2 and control RNAi1, 2, and 3. In (B) of FIG. 3, "control 1" is cells treated with only a transfection reagent, and "control 2" and "control 3" are cells treated with control shRNAi1 and shRNAi2 having the nucleotide sequences of SEQ ID NOS: 3 and 4, respectively.

Example 4

Effect of shRNAi of Syndecan-1 Gene on Tumor Cell Growth

In this Example, the shRNAi molecules constructed in Example 2 were inserted into tumor cells of endometrial cancer tissues, and degree of growth of the tumor cells was measured.

Figure 4:
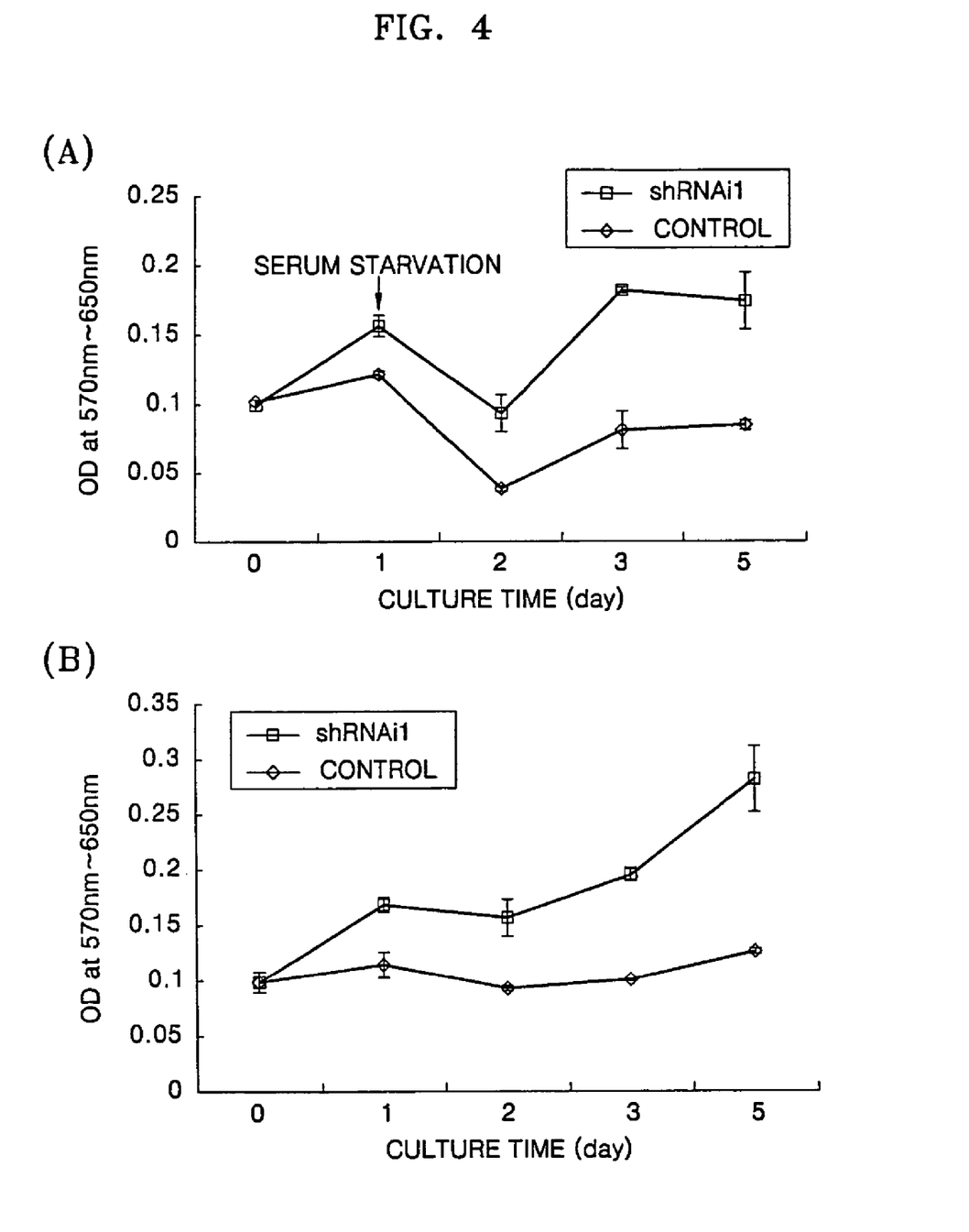
FIG. 4 illustrates MTT analysis results for shRNAi-transfected endometrial cancer cells after cultured in serum-free media (A) and in 10% FBS-containing growth media (B)

The degree of cell growth was measured using a MMT analysis method. First, the cells were grown in wells of a 96-well plate, and transfected with test shRNAi and control shRNAi. At 24 hours post-transfection, an additional growth medium was added to each well. For serum starvation, the growth media were replaced with serum-free media at one day after the transfection. After culture, the cells were allowed to form tetrazolium salts and be solubilized in a surfactant for 4 hours. Absorbance in each well was measured at 570/650 nm. The measurement results for degree of cell growth are shown in FIG. 4. In FIG. 4, (A) shows MTT analysis results in serum-free conditions and (B) shows MTT analysis results in 10% FBS-containing growth media.

Example 5

Effect of shRNAi of Syndecan-1 Gene on Tumor Cell Growth in Unattached State

In this Example, tumor cells of endometrial cancer tissues transfected with the shRNAi molecules constructed in Example 2 were cultured in an unattached state, and MTT analysis was performed to evaluate an effect of the shRNAi on the growth of the tumor cells in an unattached state.

First, a 96-well dish was coated with 1% sterilized agar in water. Then, 2,000 transfected cells were added to 200 μl of growth media in the coated wells and incubated for 8 days. 75 μl of the growth media were replaced with new ones every three days. The cultures were incubated overnight until a formazan salt was formed and then solubilized to measure an absorbance at 570/650 nm.

Figure 5:
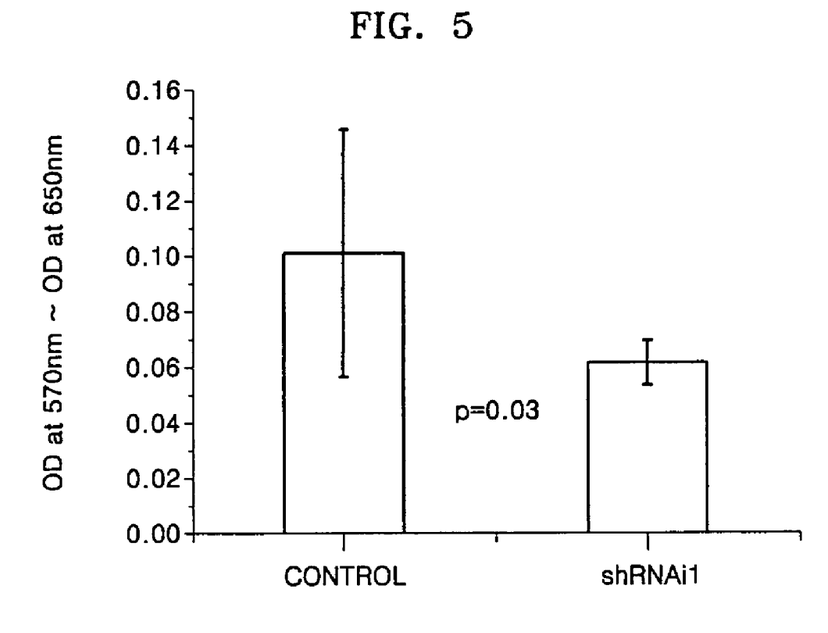
FIG. 5 illustrates MTT analysis results for shRNAi-transfected endometrial cancer cells after cultured in an unattached state.

The results are shown in FIG. 5. As shown in FIG. 5, the growth of the tumor cells in an unattached state was remarkably inhibited by shRNAi. This shows that cell growth of endometrial cancer cells is supported by syndecan-1 gene expression.

Example 6

Effect of shRNAi of Syndecan-1 Gene on Invasion of Tumor Cells

In this Example, after tumor cells of endometrial cancer tissues transfected with the shRNAi molecules constructed in Example 2 were allowed to be invaded into normal endometrial stromal cell layers, the number of invaded tumor cells was counted to evaluate an effect of shRNAi on the invasion of tumor cells into normal cells.

First, endometrial cancer cells were inoculated at a density of $5 \times 10^3$ cells onto matrigel-coated culture inserts, incubated for 24 hours, and transfected for one day. Then, the transfected cells were allowed to invade onto normal endometrial stromal cell layers in a 12-well dish and then incubated for 2 days. The number of invaded cells was counted. For this, bottom layers of the culture inserts were stained with eosin.

Figure 6:
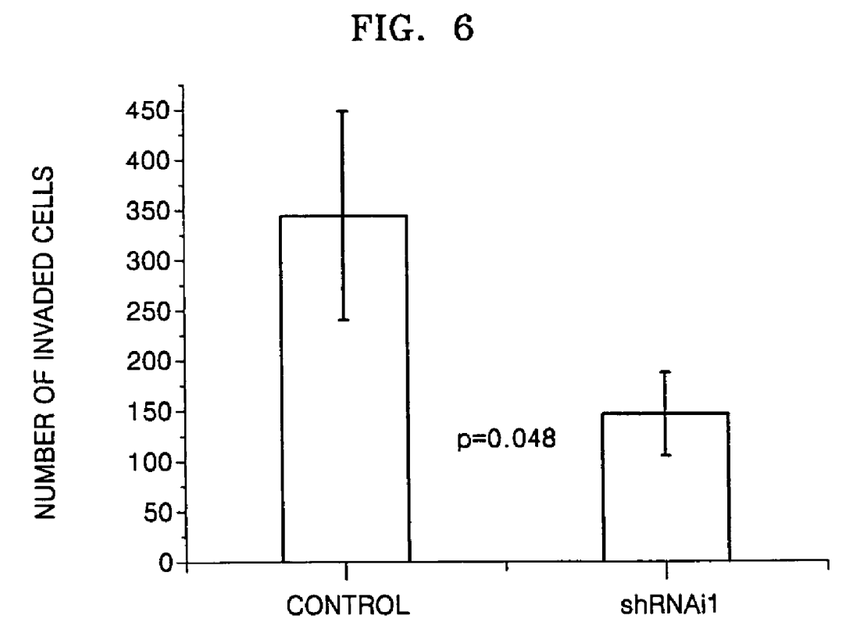
FIG. 6 illustrates the number of shRNAi-transfected endometrial cancer cells invaded into normal endometrial stromal cell layers.

The results are shown in FIG. 6. As shown in FIG. 6, the invasion of tumor cells into normal cell layers was remarkably inhibited by shRNAi. This shows that the invasion of endometrial cancer cells into normal cell layers is supported by syndecan-1 gene expression.

From these results of Examples of the present invention, it can be seen that overexpression of syndecan-1 in endometrial cancer cells facilitates invasive cell growth, thereby leading to harmful effects, which is in contrast to the results observed in many other cancers.

According to a composition for the treatment or prevention of an endometrial cancer of the present invention, an endometrial cancer can be treated or prevented by suppressing the expression of human syndecan-1 gene, unlike the facts known in other cancers.

According to a method of treating or preventing an endometrial cancer of the present invention, an endometrial cancer can be effectively treated or prevented.

What is claimed is:

1. A composition comprising a nucleic acid molecule inducing RNA interference against human syndecan-1 gene expression in cultured endometrial cancer cells in vitro and a pharmaceutically acceptable carrier, wherein said nucleic acid molecule is selected from the group consisting of an RNA of SEQ ID NO: 1, and a DNA encoding an RNA of SEQ ID NO: 1, and wherein said human syndecan-1 gene consists of the sequence of SEQ ID NO: 7.

2. A nucleic acid molecule inducing RNA interference against human syndecan-1 gene expression, wherein said nucleic acid molecule is selected from the group consisting of an RNA of SEQ ID NO: 1, and a DNA encoding an RNA of SEQ ID NO: 1, and wherein said human syndecan-1 gene consists of the sequence of SEQ ID NO: 7.

3. A method of inhibiting the growth of a human endometrial cancer cell in vitro, the method comprising administering the composition of claim 1 to a human endometrial cancer cell in vitro.

* * * * *